US006040142A

United States Patent [19]

Melki et al.

[11] Patent Number: 6,040,142

[45] Date of Patent: Mar. 21, 2000

[54] METHOD AND PROBES FOR DETECTING MARKERS LINKED TO THE INFANTILE SPINAL MUSCULAR ATROPHY LOCUS

[75] Inventors: Judith Melki; Arnold Munnich, both of Paris, France

[73] Assignee: Institut National de la Santa et de la Recherche Medicale, Paris, France

[21] Appl. No.: 08/750,064

[22] PCT Filed: Jun. 2, 1995

[86] PCT No.: PCT/FR95/00722

§ 371 Date: Jan. 29, 1997

§ 102(e) Date: Jan. 29, 1997

[87] PCT Pub. No.: WO95/33852

PCT Pub. Date: Dec. 14, 1995

[30] Foreign Application Priority Data

Jun. 3, 1994 [FR] France .................................. 94 06856

[51] Int. Cl.$^7$ ............................ C07H 21/04; C12Q 1/68; C12P 19/34

[52] U.S. Cl. ............................ 435/6; 435/91.2; 435/91.5; 536/23.5; 536/24.31; 536/24.33

[58] Field of Search ............................ 435/6, 91.2, 91.5; 536/24.31, 24.33, 23.5

[56] References Cited

FOREIGN PATENT DOCUMENTS

WO 92/00386 1/1992 WIPO .

OTHER PUBLICATIONS

Brahe et al. American Journal of Medical Genetics. 45:408–411, 1993.

Brahe et al. Human Genetics. 93:494–501, May 1994.

Burghes et al. Genomics. 21:394–402, May 1994.

Wirth et al, "Large Linkage Analysis in 100 Families with Autosomal Recessive Spinal Muscular Atrophy (SMA) and 11 CEPH Families Using 15 Polymorphic Loci in the Region 5q11.2–q13.3", Genomics 20:84–93 (1994).

Clermont et al, "Use of Genetic and Physical Mapping to Locate the Spinal Muscular Atrophy Locus between Two New Highly Polymorphic DNA Markers", Am. J. Hum. Genet. 54:687–694 (1994).

Brzustowicz et al, "Paternal Isodisomy for Chromosome 5 in a Child with Spinal Muscular Atrophy", Am. J. Hum. Genet. 54:482–488 (1994).

Thompson et al, "High resolution physical map of the region surrounding the spinal muscular atrophy gene", Human Molecular Genetics 2(8):1169–1176 (1993).

Huschenbett et al, "Prenatal Diagonosis of the Acute Form of Proximal Spinal Muscular Atrophy: Experience on the Acceptance of Linkage Analyses by the Families", Prenatal Diagnosis 13:643 (1993).

Melki et al, "De Novo and Inherited Deletions of the 5q13 Region in Spinal Muscular Atrophies", Science 264:1474–1477 (1994).

*Primary Examiner*—Carla J. Myers
*Attorney, Agent, or Firm*—Nixon & Vanderhye P.C.

[57] ABSTRACT

The invention relates to methods and compositions for detecting the presence of genetic alterations in the human 5q13 chromosomal region. More specifically, the invention relates to nucleic acids, probes, primers, and methods of using the same, for the amplification and/or the detection of alterations in the human 5q13 chromosomal region, and their correlation to spinal muscular atrophy.

16 Claims, 5 Drawing Sheets

METHOD AND PROBES FOR DETECTING MARKERS LINKED TO THE INFANTILE SPINAL MUSCULAR ATROPHY LOCUS

Infantile spinal muscular atrophy (SMA) represents the commonest group of fatal autosomal recessive hereditary disorders after cystic fibrosis (incidence: 1/6,000) (1). SMA is characterized by a degeneration of the motor neurones of the anterior horn of the spinal cord, leading to a progressive paralysis of the limbs and trunk associated with a muscular atrophy. Infantile spinal muscular atrophy is divided into categories termed types I, II and III, according to the age of onset of the symptoms and the manner of their progression (2).

It should be noted that type I spinal muscular atrophy is observed only in newborn babies and in infants: it is the most serious type, the life expectancy of these children barely exceeding a few years.

Type II spinal muscular atrophy also manifests itself as early as the first year of life of the children affected, but after they have acquired the ability to sit. They can then barely get up any longer,. and at best reach the stage of adolescence.

Lastly, type III spinal muscular atrophy appears in children when they begin to walk; the symptoms described above then develop more slowly.

Apart from diagnosis based on clinical and paraclinical signs (electromyography and muscle biopsy) of appearance of the disease, signs which often do not afford the requisite specificity, there hardly exist any other methods permitting an equivalent diagnosis, be it only in a limited number of cases. It goes without saying that the clinician, called upon to anticipate the future appearance of the disease in patients presumed to be at risk or, in neonatal medicine, in the fetus, is even more helpless.

The biochemical abnormality of this disorder is unknown. Nevertheless, the gene responsible for the three forms of SMA has been localized by genetic linkage analysis on chromosome 5q11.2–q13.3 (3–6), so that the disorders in question would appear to be alleleic.

Recently, the gene responsible for SMA has been localized on chromosome 5 within a span of 2 centimorgans (cM) defined by the flanking loci D5S629 and D5S637 (7).

Several fragments originating from this chromosome have been cloned in yeast artificial chromosomes or YACs. Several contigs of YACs of the 5q13 region have been described. The expression "contig of the 5q13 region" relates to a set of YACs in which the inserts formed from fragments of the 5q13 region may be considered to overlap one another, this set of fragments nevertheless spanning the whole of the 5q13 region. One of these contigs consisted of 7 overlapping YACs covering approximately 3.2 Mb (13), the other of 10 overlapping YACs covering a region of 2 Mb (14). However, none of the markers known to date enables a correlation to be established, be it only partial yet reliable, between the detection which can be performed using them and the clinical signs of the disease.

The invention is based more especially on the discovery that the 5q13 region contained several loci which, setting aside repeat sequences which varied in number, possessed substantially identical nucleotide sequences and formed a similar number of polymorphic markers characteristic of this region. The polymorphism of these markers is the source of the capacity of researchers to distinguish between them, to correlate them sometimes with those carried by the parents of the subjects under study, or on the contrary to identify the de novo character of the mutations or deletions to which they may be subjected. This polymorphism is also the source of the capacity now possessed by researchers in a number of cases, either to find therein the confirmation of the correct nature of a clinical diagnosis of SMA, in particular of type 1, or sometimes to rule it out, for example in neonatal medicine and when there is a history of the disease in a brother or sister.

These new DNA markers, more especially polymorphic markers (microsatellites), were identified by screening fragments contained within the abovementioned span of two cM identified by (7) and contained in a YAC of 4 Mb. This screening was performed by employing a library of YACs of the Centre d'Etudes du Polymorphisme Humain (CEPH), [Center for Human Polymorphism Studies], Paris, France, using the first-generation YACs 755B12 (containing the marker AFM265wf5) and 751E3 (containing the marker AFM 281yh9), by PCR amplification between the primers specific for each marker according to the three-dimensional (3d) method described previously (8). Chromosome walking according to a method described previously (12) enabled new YACs overlapping the previous YACs and containing the new polymorphic DNA markers (microsatellites) to be identified.

The procedure was, in particular, as follows.

Families

The high resolution genetic map previously prepared had made it possible to recognize recombination events between the SMA locus and the closest flanking polymorphic loci (D5S629 and D5S637) (7). Genetic analysis of the nine families containing key recombinations was carried out with the new polymorphic markers. The families in question were either consanguineous (n=5) or families containing several affected subjects (n=4). This genetic analysis consisted in constructing the most probable haplotypes, established by minimizing the number of meiotic recombination events.

Screening of the YAC Libraries

The YAC libraries of the CEPH were screened by PCR amplification between the primers specific for each marker according to the three-dimensional (3d) method described previously (8). The genotype of the YACs containing the microsatellite markers was established by electrophoresis of the PCR products on denaturing polyacrylamide gel, transferred onto a charged nylon membrane and hybridized with a $^{32}$P-labelled oligonucleotide (CA)n or (CT)n. Detection of the dinucleotide repeats was performed by a method described (9). The size of the YACs was estimated after pulsed-field electrophoresis.

Generation of the Markers From the YACs Selected

The DNA of the YACs was separated from the yeast chromosomes after pulsed-field electrophoresis on agarose gel, known under the brand name "SEAPLAQUE GTG 1%". After treatment with b agarase, the DNA was precipitated in ethanol. A total of 300 ng of YAC was digested with the restriction enzyme Sau 3A and then partially repaired before being cloned into bacteriophage M13 at the partially repaired Sal 1 [sic] site.

The M13 clones containing (CA) or (CT) repeats were detected by means of targeting with the $^{32}$P-labelled oligonucleotides (CA) 20 or (CT) 20. The positive templates were then sequenced (10). Oligonucleotide primers flanking the (CA) or (CT) repeats were chosen. The chromosomal localization of the markers was determined after PCR amplification of the DNAs of a panel of somatic hybrids of chromosome 5. This panel contains the line HHW105 containing as unique human chromosome the whole chromosome 5, the line HHW1064 containing chromosome 5 deleted in the 5q11–q14 region and the line HHW213 containing chromosome 5p (11). The polymorphic loci were recognized by testing 5 unrelated control individuals. The nonpolymorphic markers were used as STSs (abbreviation for the expression "sequence tagged site" or sequence labelled site)

Chromosome Walking

This walking utilized, starting from the selected YACs, the PCR amplification products generated between the oligonucleotide A33 chosen from the moderately repeated ALU type sequences. These products enabled new YACs overlapping the previous ones to be selected according to the method described previously (12). New polymorphic DNA markers were then isolated again from these YACs.

This chromosome walking enabled new YACs overlapping the previous ones to be identified, and new DNA markers were then isolated. Of the 28 markers identified, 9 were excluded from the study since they were also present on the short arm of chromosome 5, demonstrating the existence of a partial duplication of the 5q13 region on chromosome 5p (Table 1).

The 19 markers specific for the 5q13 region were used to select potentially overlapping YACs. Nine of them detect more than one locus in the 5q13 region (Table 1). In effect, four polymorphic microsatellite markers [C212 (D5F149S1-S2), C271 (D5F148S1-S2), C272 (D5F150S1-S2), C171 (D5F151S1-S2)] revealed the presence of two amplification products, and one marker [C161 (D5F153S1-S2-S3)] revealed 3 amplification products on the somatic hybrid HHW105. None of them were localized outside the 5q13 region. These results demonstrate that the markers C212, C272, C271, C171 detect 2 loci and the marker C161 detects three loci in the 5q13 region. These results show the presence of repeat elements on chromosome 5q13 (Table 1).

As a result of the complex genomic organization of this region, these polymorphic loci were used to select the overlapping YACs, and to genotype them with respect to the DNA of the donor in order to make sure that the whole of the region was covered. Confirmation of this genomic organization was provided by the identification of a YAC (903D1) whose genotype is identical to those of the YACs 595C11 and 759A3. The YAC contig contains a minimum of 5 YACs covering approximately 4 megabases from the marker AFM265wf5 to the marker AFM281yh9 (FIG. 1).

High Resolution Genetic Mapping at the SMA Locus

Based on the conventional analysis of the haplotypes and on the method of homozygosity by descent, 10 key recombinant meioses were selected. Genetic analysis of these recombinant meioses was carried out with the new polymorphic markers isolated from the YAC contig (FIG. 1). The most polymorphic markers C212 and C272 no longer reveal any recombination event with the SMA locus. These results demonstrate that these markers detect the loci closest to the SMA gene.

The invention relates more especially to means (nucleic acids and methods) enabling several of these polymorphic markers to be detected and, if appropriate, to be distinguished from one another.

In particular, it relates to DNA strands, each of which is characterized in that its own nucleotide sequence:

- is contained in the nucleic acid sequence of one of the strands of a polymorphic marker of a human chromosomal region deemed to contain an SMA locus, this marker containing a variable number of repeat sequences, in particular of dinucleotide repeats;
- itself contains a characteristic sequence present in this polymorphic marker but outside the region of the latter which contains said repeat sequences, this characteristic sequence being of sufficient size, in particular of at least 12 and preferably at least 15 nucleotides, for a fragment of the same sequence to be useable as primer for the detection by PCR of corresponding markers in a DNA preparation of human origin.

Among preferred strands of the invention, mention will be made of those whose own sequence—or the sequence which is complementary thereto—consists of all or part of one of the regions outside the region containing the repeat sequences, which regions are contained, respectively, in one of the DNA sequences identified below under the designations C212, C272, AFM157, C161 and C171.

C212 (D5F149S1, S2), hereinafter "C212" (SEQ ID NO:1)

```
ACCTGANCCCAGANGGTCAAGGCTGCAGTGAGACGAGATTGCNCCACTGCCCTCC
ACCCTGGGTGATAAGAGTGGGACCCTGTNTCAAAACATACACACACACACACACA
CACACACACACACACACACACACACTCTCTCTCTCTCTCTCTCTCTCTCTCTCTC
TCTCTCTCTCTCTCAAAAACACTTGGTCTGTTATTTTTNCGAAATTGTCAGTCAT
AGTTATCTGTTAGACCAAAGCTGNGTAAGNACATTTATTACATTGCCTCCTACAA
CTTCATCAGCTAATGTATTTGCTATATAGCAATTACATATNGGNATATATTATCT
TNAGGGGATGGCCANGTNATAAAACTGTCACTGAGGAAAGGA
```

C272 (DSF150S1, S2), hereinafter "C272" (SEQ ID NO:2)

```
CCTCCCACCTNAGCCTCCCCAGTAGCTAGGACTATAGGCGTGCNCCACCAAGCTC
AGCTATTTTTNNTATTTAGTAGAGACGGGGTTTCGGCANGCTTAGGCCTCGTNTC
GAACTCCAGTGTGTGTGTGTGTGTGTGTGTGTGTGTGTGTGTGTGTGTGTGTGTG
```

-continued

TGTGTAGATATTTATTCCCCCTCCCCCTTGGAAAAGTAAGTAAGCTCCTACTAGG

AATTTAAAACCTGCTTGATCTATATAAAGACAAACAAGGAAAGACAAACATGGGG

GCAGGAAGGAAGGCAGATC

AFM157xd10 (SEQ ID NO:3)

TCGAGGTAGATTTGTATTATATCCCATGTACACACACACACACACACACACAC

ACACACACACACAGACTTAATCTGTTTACAGAAATAAAAGGAATAAAATACCGTT

TCTACTATACACCAAAACTAGCCATCTTGAC

C161 (D5F153S1, S2, S3), hereinafter “C161” (SEQ ID NO:4)

CCCTGAGAAGGCTTCCTCCTGAGTATGCATAAACATTCACAGCTTGCATGCGTGT

GTGTGTGTGTGTGTGTGTGTATGTTTGCTTGCACTGTAAAAACAATTGCAACATC

AACAGAAATAAAAATTAAAGGAATAATTCTCCTCCGACTCTGCCGTTCCATCCAG

TGAAACTCTTCATTCTGGGGTAAAGTTCCTTCAGTTCTTTCATAGATAGGTATAT

ACTTCATAAGTCAAACAATCAGGCTGGGTGCAGTAGCTCATGCCTGTAATCCCAG

CCCTTTGGGAGGCCGAGCTGGGCAGATCGA

C171 (D5F151S1, S2), hereinafter “C171” (SEQ ID NO:5)

TCCACCCGCCTTGGCCTCCCAAAGCNCTGGGATTACAGGCGTGACTGCCGCACCC

AGCTGTAAACTGGNTTNNTAATGGTAGATTTTNAGGTATTAACAATAGATAAAAA

GATACTTTTNGGCATACTGTGTATTGGGATGGGGTTAGAACAGGTGTNCTACCCA

AGACATTTACTTAAAATCGCCCTCGAAATGCTATGTGAGCTGTGTGTGTGTGTGT

GTGTGTGTGTGTATTAAGGAAAAGCATGAAAGTATTTATGCTTGATTTTTTTTTT

TNACTCATAGCTTCATAGTGGANCAGATACATAGTCTAAATCAAAATGTTTAAAC

TTTTTATGTCACTTGCTGTC

These DNA strands, most particularly if they are long enough, may be used as direct probes, for example for the presence or otherwise of a deletion in the corresponding marker. The invention then also relates, in this case, to recombinant DNAs (single-stranded or double-stranded) containing this strand recombining with a nonhuman nucleic acid and not capable of hybridizing with a fragment of human DNA.

However, preferably, preferred strands are those which can be used in a chain amplification method, in particular of the PCR (abbreviation for the expression “polymerase chain reaction”, or chain reaction in the presence of a polymerase) type.

In particular, the invention relates to the primer pairs, preferably containing at least 12 and advantageously at least 15 nucleotides, whose sequences are contained, respectively, in the pairs of sequences originating, in particular, from:

- C212

(1) ACCTGANCCCAGANGGTCAAGGCTGCAGTGAGACGAGATTGCNCCACTGCC

CTCCACCCTGGGTGATAAGAGTGGGACCCTGTNTCAAAACATA (2) sequence ccmplementary to: (SEQ ID NO:7)

CAAAAACACTTGGTCTGTTATTTTTNCGAAATTGTCAGTCATAGTTATCTG

TTAGACCAAAGCTGNGTAAGNACATTTATTACATTGCCTCCTACAACTTCA

TCAGCTAATGTATTTGCTATATAGCAATTACATATNGGNATATATTATCTT

NAGGGGATGGCCANGTNATAAAACTGTCACTGAGGAAAGGA

-continued or vice versa

- C272

(1) CCTCCCACCTNAGCCTCCCCAGTAGCTAGGACTATAGGCGTGCNCCACCAA

GCTCAGCTATTTTTNNTATTTAGTAGAGACGGGGTTTCGGCANGCTTAGGC

CTCGTNTCGAACTCCA (SEQ ID NO:8)

(2) sequence complementary to (SEQ ID NO:9):

AGATATTTATTCCCCCTCCCCCTTGGAAAAGTAAGTAAGCTCCTACTAGGA

ATTTAAAACCTGCTTGATCTATATAAAGACAAACAAGGAAAGACAAACATG

GGGGCAGGAAGGAAGGCAGATC or vice versa

- AFM157xd10

(1) TCGAGGTAGATTTGTATTATATCCCATGTA (SEQ ID NO:10)

(2) sequence complementary to (SEQ ID NO:11):

CTTAATCTGTTTACAGAAATAAAAGGAATAAAATACCGTTTCTACTATACA

CCAAAACTAGCCATCTTGAC or vice versa

- C161

(1) CCCTGAGAAGGCTTCCTCCTGAGTATGCATAAACATTCACAGCTTGCATGC (2) seqence complementary to (SEQ ID NO:13):

ATGTTTGCTTGCACTGTAAAAACAATTGCAACATCAACAGAAATAAAAATT

AAAGGAATAATTCTCCTCCGACTCTGCCGTTCCATCCAGTGAAACTCTTCA

TTCTGGGGTAAAGTTCCTTCAGTTCTTTCATAGATAGGTATATACTTCATA

AGTCAAACAATCAGGCTGGGTGCAGTAGCTCATGCCTGTAATCCCAGCCCT

TTGGGAGGCCGAGCTGGGCAGATCGA or vice versa

- C171

(1) TCCACCCGCCTTGGCCTCCCAAAGCNCTGGGATTACAGGCGTGACTGCCGC

ACCCAGCTGTAAACTGGNTTNNTAATGGTAGATTTTNAGGTATTAACAATA

GATAAAAAGATACTTTTNGGCATACTGTGTATTGGGATGGGGTTAGAACAG

GTGTNCTACCCAAGACATTTACTTAAAATCGCCCTCGAAATGCTATGTGAG

CT (SEQ ID NO:14)

(2) sequence complementary to (SEQ ID NO:15):

ATTAAGGAAAAGCATGAAAGTATTTATGCTTGATTTTTTTTTTTNACTCAT

AGCTTCATAGTGGANCAGATACATAGTCTAAATCAAAATGTTTAAACTTTT

TATGTCACTTGCTGTC or vice versa it naturally being understood that the expression "vice versa" means that each of the primers originating from the abovementioned pairs of sequences (1) and (2) could be replaced by a complementary primer.

As examples of preferred primer pairs corresponding to the abovementioned families, the following oligonucleotides may be mentioned:

C212A (SEQ ID NO:16): CCTCCACCCTGGGTGATAAG

C212B (SEQ ID NO:17): GCTGATGAAGTTGTAG-GAGGC
C272A (SEQ ID NO:18): TAGAGACGGGGTTTCGGCAT
C272B (SEQ ID NO:19): GATCTGCCTTCCTTCCTGC
C161A (SEQ ID NO:20): GGCTTCCTCCTGAGTATGCA
C161B (SEQ ID NO:21): GTTTCACTGGATGGAACGGC
C171A (SEQ ID NO:22): ATCGCCCTCGAAATGCTATG
C171B (SEQ ID NO:23): CTGTTCCACTATGAAGCTATG

The invention naturally relates also to DNA strands which may be considered to be complete replicas of the corresponding markers, it also being possible for these strands (which then also contain the corresponding repeat sequences) to be used as specific probes for the corresponding markers, for example for purposes of verifying the existence or otherwise of this specific marker on one of the allelees of a chromosome under study.

The invention also relates to a method for studying the chromosomal region deemed to contain at least one of the genes involved, either by its presence or by its absence, in SMA and originating from a subject (patient or fetus) affected or liable to be affected, this method comprising bringing a chromosomal DNA sample of this subject or fetus into contact with at least one of the DNA strands as defined above, in particular under amplification conditions permitting, provided it would hybridize with corresponding markers of this chromosomal DNA, the elongation of its chains towards and beyond the repeat sequences of these markers, and then implementing conditions enabling a distinction to be made between the elongation chains obtained according to their respective lengths in order to obtain data representative of the number of these markers.

The procedure preferably used will be PCR, the chromosomal DNA sample then being brought into contact with a primer pair as defined above, capable of hybridizing with the regions of the markers outside the ones which contain their respective repeat sequences, the elongation chains produced then being distinguished from one another, in particular by their migration in a suitable electrophoresis gel.

The result, in particular of the experiments the results of which will be reported later, is that, in an appreciable percentage of cases, the existence of or potential for an SMA, in particular of type 1 manifests itself in a smaller number of polymorphic markers detected than are observed in chromosomal DNAs originating from healthy subjects, this reduction indicating that, in affected subjects, essential portions of the 5q13 region have, in fact, been deleted.

In preferred embodiments of the invention, applied, more especially, to subjects at risk, in particular on account of the present or past existence of other cases of SMA in the same family, the method according to the invention will also and for comparative purposes be carried out on chromosomal preparations originating from the parents or other related persons.

The experiments the results of which are described below tend to show that those subjects who have received from both parents an allele containing a marker which has given rise to chain elongation are less at risk of SMA, in particular of type 1, than those who have received only one of them or those in whom one of the alleles does not carry such a marker.

As a result of polymorphism of the markers employed, it is, in effect, possible to discern, in particular by means of the differing migrations of the amplification products due to their different sizes, those alleles carrying a marker inherited, where appropriate, from one of the parents and those inherited, where appropriate, from the other, or alternatively, as the invention has enabled it to be established, the appearance of de novo deletions with the consequent risk of appearance of the disease in subjects whose parents did not apparently evince any predisposition for them.

Conversely, the detection in a given subject, in particular in the fetus, of the presence of at least one polymorphic marker on each of the alleles of the corresponding chromosome, in particular when the comparative study will enable it to be concluded that the fetus has inherited these markers from both of its respective parents and that the subject is not predisposed to the disease. The same could apply in the case of young children, every time the clinical signs they present lead the clinician to ponder the possibility they might have of developing the disease.

The importance of the result which the invention makes it possible to obtain, at least in a number of cases, will then be understood, be it only to check, in neonatal medicine, for the absence of genetic potential for the disease in the fetus, or to confirm a negative diagnosis in the young child whereas some clinical signs were appearing to point towards the contrary.

The invention and the results which it makes it possible to obtain are further illustrated in greater detail—and without implied limitation—in what follows. Reference will also be made to the drawings and the table, which may be interpreted by reference to the legends which appear at the end of the present description.

FAMILIES AND METHODS

Families

Two hundred and one SMA families were studied. They were selected according to the diagnostic criteria adopted by the International Consortium on SMAs (15). Subjects having a confirmed SMA were divided into three subgroups (type I, II or III). Ninety patients belonged to type I, 81 to type II and 30 to type III. Two large reference families of the CEPH, 22 healthy families composed of both parents and a child, and 60 unrelated healthy individuals were used as controls. For the purposes of the statistical analysis, only one affected child per family was included in the study.

METHODS

Southern Blotting

The DNA of the different individuals was extracted from pellets of leukocytes or of lymphoblastoid lines. It was then digested with different restriction enzymes and thereafter put to migrate on 0.8% agarose gel before being transferred onto a charged nylon membrane.

Detection of the Dinucleotide Repeat Polymorphisms

From the same DNAs, a PCR amplification was carried out between the primers specific for the markers C212 (D5F149S1 and S2), C272 (D5F150S1 and S2) and C161 (D5F153S1, S2 and S3). The amplification conditions are as follows: denaturation at 94° C. for 1 min, hybridization at 55° C. for 1 min and extension at 72° C. for 1 min for 30 cycles. The PCR products are then put to migrate on denaturing polyacrylamide gel, and transferred onto a positively charged nylon membrane which is hybridized with a probe that recognizes the dinucleotide repeats CA (20).

Construction of a Library of Phages from YAC 595C11

After partial digestion with the enzyme Sau 3A, the DNA of the clone 595C11 was applied to and put to migrate on agarose gel (known by the designation "SEAPLAQUE GTG 0.5%"). After migration, the fragments 12 to 23 Kb in size are cut out, digested with b-agarase and then precipitated in ethanol. After partial repair of the Sau 3A site, the DNA is subcloned at the partially repaired Xho 1 site of the bacteriophage FIX II (Stratagene). The lambda clones containing the markers C212 (L-51), C272 (L-51, L-132) and C171 (L-5, L-13) were used as probes to test for restriction polymorphisms (RFLP) with the restriction enzymes EcoR I, Bgl II, Hind III and Xba I. The probe JK53 (D5S112) was used as internal control for the gene dosage analyses. The autoradiographs were examined by densitometry at 600 nm (Hoefer Scientific Instruments, San Francisco).

RESULTS

To test the hypothesis according to which the presence of repeat elements could favor the occurrence of rearrangements in the patients, the segregation of the alleles was analyzed at the loci detected by the markers C212 and C272 in 201 nonconsanguineous SMA families. A parental noncontribution to these loci in eight affected children belonging to seven unrelated families. Four patients were affected by the type I, two by the type II and two by the type III form. The absence of parental contribution was of maternal origin in five of the cases (families 3, 4, 5, 6) and of paternal origin in the other three (families 1, 2, 7; FIG. 1). One of the type I patients displayed a rearrangement occurring de novo removing only one of the two loci recognized by the markers C212 and C272 (FIG. 1, family 7). Identical results were obtained using different oligonucleotide pairs for each of the markers. Construction of the haplotypes using markers flanking the SMA locus (21) enabled the hypothesis of a false paternity or a sampling error to be ruled out. These results indicate the presence of rearrangements removing the morbid locus in these eight patients.

Furthermore, because it had been possible to underestimate the number of patients displaying a rearrangement through a lack of data concerning the meioses, the number of distinct PCR amplification products revealed by the markers C212 and C272 was analyzed in the SMA families of the three types, as well as in 60 controls composed of unrelated individuals (FIG. 2). In 16 of the 90 type I patients (18%), a single PCR amplification product with the marker C272 was detected, a statistically very different result from the one observed in the type II patients (1/81, equivalent to 1%), the type III patients (1/30, equivalent to 3%) and the controls (0/59, equivalent to 0%, $p<0.001$). Similarly, the proportion of type I patients displaying two PCR amplification products (55/90, equivalent to 61%) is also significantly different from that of the parents (69/180, equivalent to 38%) and of the controls (12/59, equivalent to 20%, $p<0.001$) . Similar results were obtained with the marker C212 (Table). The possibility that the reduction in the number of amplified fragments in the types I could be due to a distant consanguinity was ruled out by comparison of the number of fragments shared by the parents of the subjects affected by SMA and that of the parents of 20 unrelated control families. The results then showed no statistically significant difference (data not shown).

The 20 type I families whose affected child displayed only one PCR amplification product with the markers C212 or C272 were then analyzed with the marker C161. In two of the twenty families, we observed a rearrangement occurring de novo and removing 2 of the 3 loci detected with the marker C161 (FIG. 3, families 8 and 9). These results clearly support the hypothesis according to which the alleleic reduction at the loci detected with the markers C212 and C272 in type I SMAs is due to a loss of allele at these loci. To characterize the extent of the 5q13 region deleted in these patients, these families were analyzed with the other polymorphic markers generated from the new contig of YACs. Complete haplotyping of these families enabled us to map the different deletions and to delimit the boundaries of the smallest reorganization between the markers C161 and C212-C272 (FIG. 4). These results suggest that the SMA locus lies in a region of 1.2 Mb contained in the YAC 903D1 (20, 23). However, because of the perfect sequence homology of the regions flanking the CA repeats of the markers C212 and C272, it was not possible to determine which of the two loci was lacking in the single patient displaying the loss of only one locus (family 7, FIGS. 1 and 4). To provide physical proof of the presence of deletions in the 5q13 region the clone L-132, which contains the marker C272, was used as probe for the Southern blot analysis of the SMA families showing an abnormal parental contribution. Analysis of the RFLPs and of the gene dosage then confirmed the presence of inherited or de novo deletions (FIG. 5).

DISCUSSION AND CONCLUSION

The present study provides genetic and direct physical proof of the existence of deletions encompassing the locus of the disease in 10 affected children belonging to 9 unrelated families. Furthermore, the presence of deletions of the 5q13 region is strongly supported by the observation of an alleleic reduction statistically associated with the severe form of the disease (type I). Deletions are also encountered occasionally in type II or III patients. Distinct alleleic mutations could hence explain the variable clinical expression of the disease. These results also confirm that the gene or genes responsible for the three types of SMA do indeed lie in the same region. Duchenne's or Becker's muscular dystrophy may also result from deletions but, in this case, there is a mechanistic difference between the types of deletions (25), whereas such an analysis is not yet rendered possible in the SMAs. This study also demonstrates that the deletions may take place de novo, a characteristic which could explain the small coefficient of segregation previously reported by several authors in the SMAs (26, 27) and hitherto rather poorly understood. De novo deletions of the 5q13 region may also explain the apparent genetic heterogeneity of the SMAs (18, 28) when, in the same family, a healthy child displays the same haplotype as the affected child with the flanking markers. This observation is also important for genetic counselling. In effect, the apparent haplotypic identity between a fetus and the affected child of the same family, determined by means of the flanking markers, may lead to errors in prenatal diagnosis when a de novo deletion occurs. The presence of repeat elements in the 5q13 region may explain the instability of this region, thereby contributing to the appearance of deletions in subjects affected by SMA through unequal crossing-over events.

It should be noted that the C272 sequence is apparently contained in a DNA fragment (designated L132) capable of revealing the presence, either of inherited deletions or of de novo deletions, by Southern blot analysis of the length polymorphisms of the restriction fragments or by analysis of the gene dosage (dosage of a certain level of deterioration of a gene as a result of the weakening of a hybridization signal given by a probe capable of recognizing it,

TABLE 1

| Markers Status | Type (n) Number | PCR products of distinct amplifications | | | |
|---|---|---|---|---|---|
| 1 | 2 | 3 | 4 | | |
| C212 | I | 13% | 13% | | |
| Affected | (90) | 66.5% | 6.5% | | |
| I I | 2.5% | 35.5% | 59% | 2.5% | |
| (76) | | | | | |
| I I I | 3% | 23% | 66.5% | 6.5% | |
| (30) | | | | | |
| Parents | I | 1.5% | 42% | 45.5% | 10.5% |
| | (180) | | | | |
| I I | .5% | 30% | 53% | 16% | |
| (150) | | | | | |
| I I I | 0 | 23.5% | 52.5% | 23.5% | |
| (59) | | | | | |
| Controls | (60) | 0 | 18% | 60% | 21.5% |
| C272 | I | 18.5% | 15.5% | | |
| Affected | (90) | 61% | 4.5% | | |
| I I | 1% | 34% | 63% | 1% | |
| (81) | | | | | |
| I I I | 3% | 33% | 46.5% | 16.5% | |
| (30) | | | | | |
| Parents | I | 1.5% | 38.5% | 47.5% | 11.5% |
| | (180) | | | | |
| I I | .5% | 33% | 53% | 13% | |
| (162) | | | | | |
| I I I | 1.5% | 22% | 44% | 32% | |
| (59) | | | | | |
| Controls | (59) | 0 | 20% | 54% | 25% |

Table 1. Number of distinct PCR amplification products observed with the markers C212 and C272 in subjects affected by type I, II and III SMA, their parents and controls. (n) indicates the number of individuals tested.

A). Genomic map of the 5q13 region. The different markers are indicated above their genetic position. The brackets enclosing the blocks C212-C272-C171 indicate that the order of the markers inside the block is unknown.

B). Genetic map of the deletions. The short lines correspond to the markers mentioned above.

In the family 7, the deletion may involve either the centromeric block C212-C272-C171 or the telomeric block.

Figure 1A:
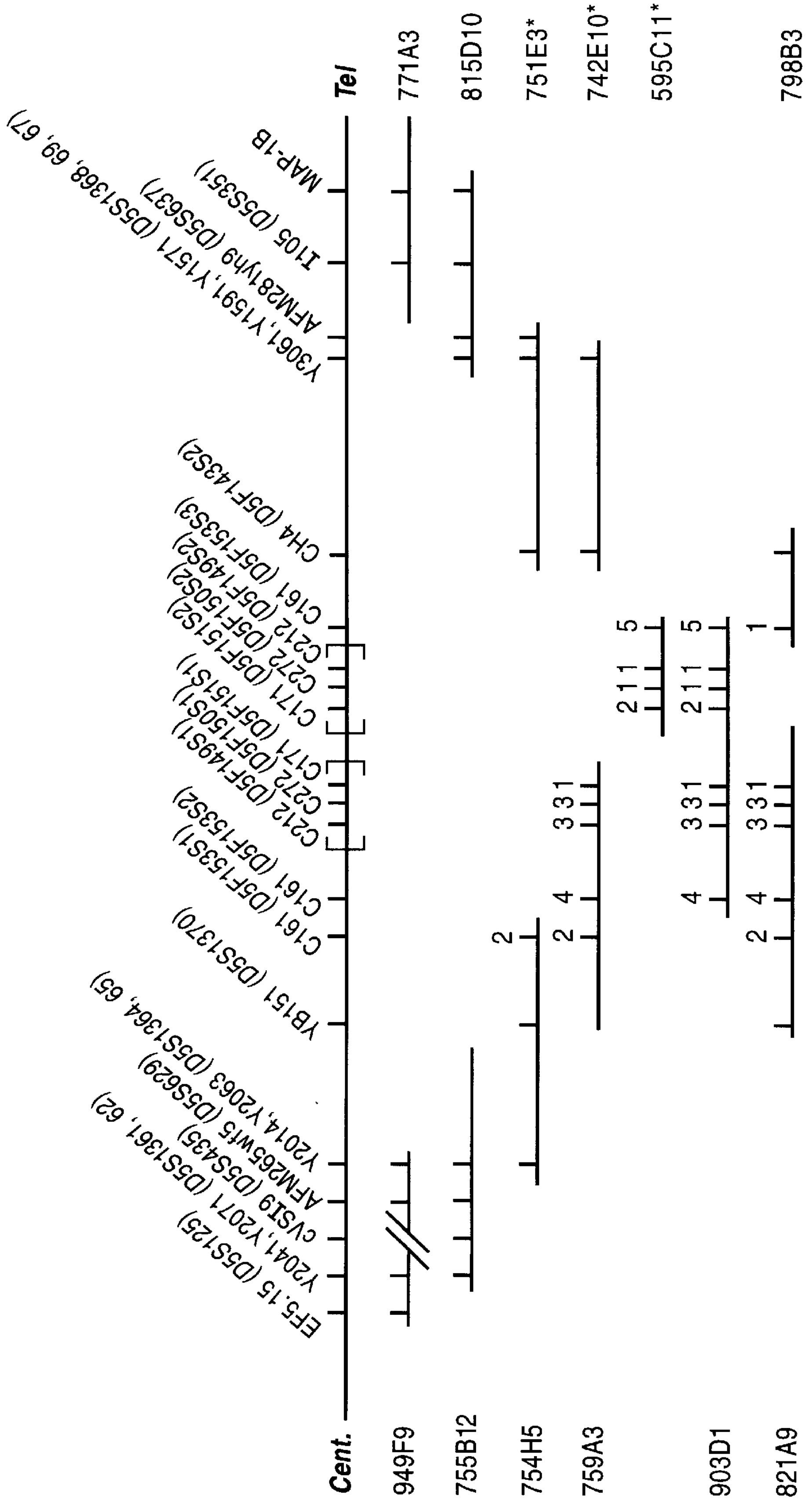
FIG. 1: Genetic map of the deletions in patients affected by SMA.
Figure 1B:
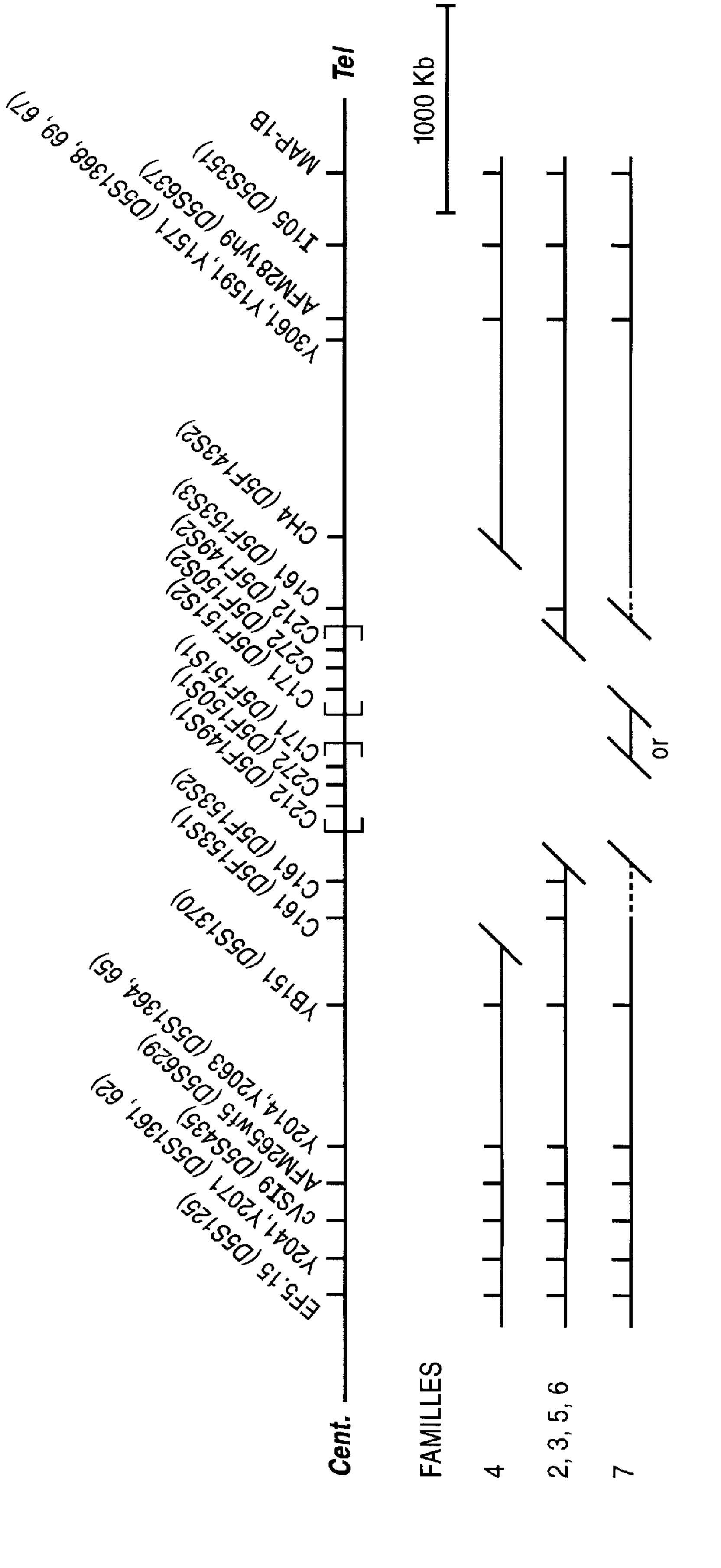
Figure 2A:
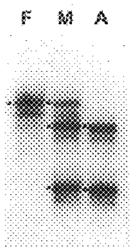
Figure 2B:
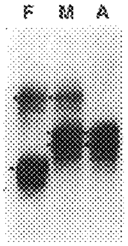
Figure 2C:
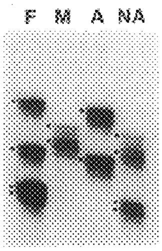
Figure 2D:
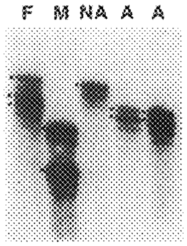
Figures 1, 4A:
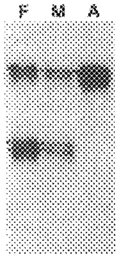
Figures 2, 4A:
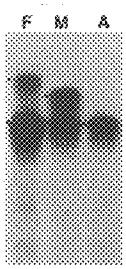

FIG. 2: Contribution of the parental alleles in patients affected by SMA, determined by the markers C212 and C272. The figure shows the study of the families either with the marker C272 (families 1, 2, 5 and 7*b*) or with the marker C212 (families 3, 4, 6 and 7*a*). The patients are affected by the type I (families 3, 5, 6 and 7), type II (families 1 and 2) or type III (family 4) form. Construction of the haplotypes with the markers flanking the SMA locus (11) enabled us to determine that the healthy children of the families 4 and 5 had received the mutated allele from their mother. In the family 7, the incomplete contribution of the father to his affected child with the markers C212 (7a) and C272 (7b) is noted, compared to the haplotypically identical fetus, as established with the flanking markers (data not shown). F: father, M: mother, A: affected, NA: nonaffected, Fe: fetus. The points indicate the alleleic fragments.

Figures 3, 4A:
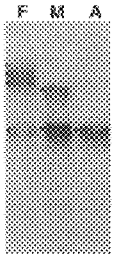
Figure 2E:
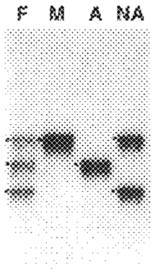
Figure 2F:
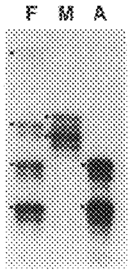
Figure 2G:
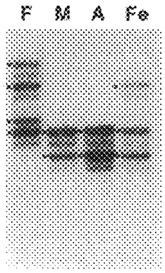
Figure 2H:
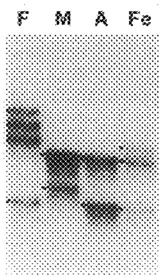
Figures 1, 4B:
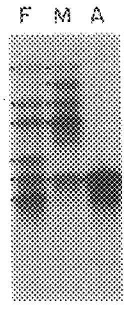
Figures 2, 4B:
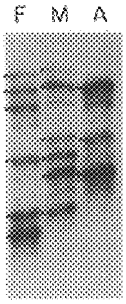
Figures 3, 4B:
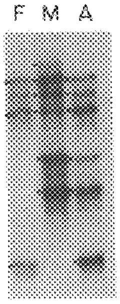
Figure 3A:
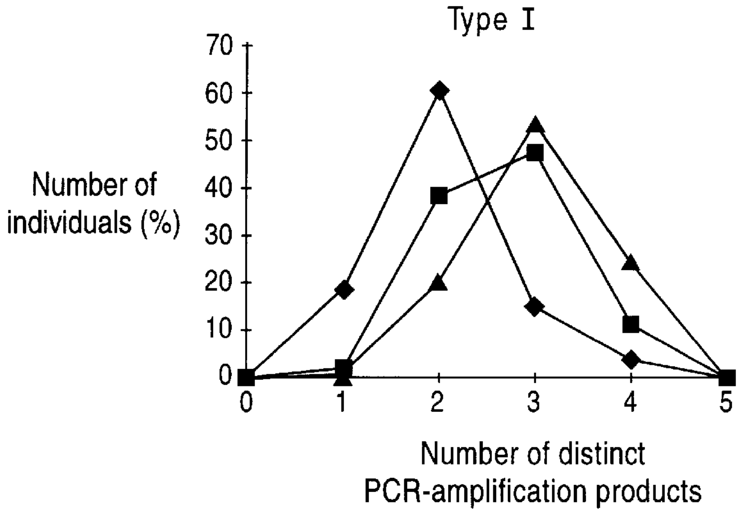
Figure 3B:
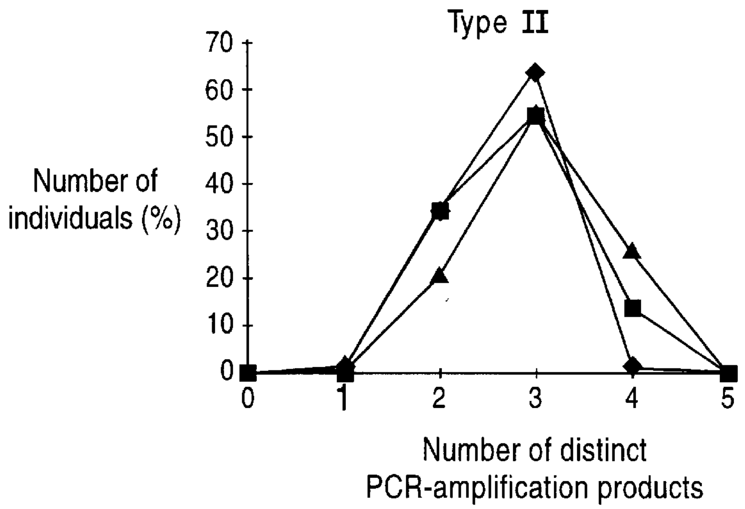
Figure 3C:
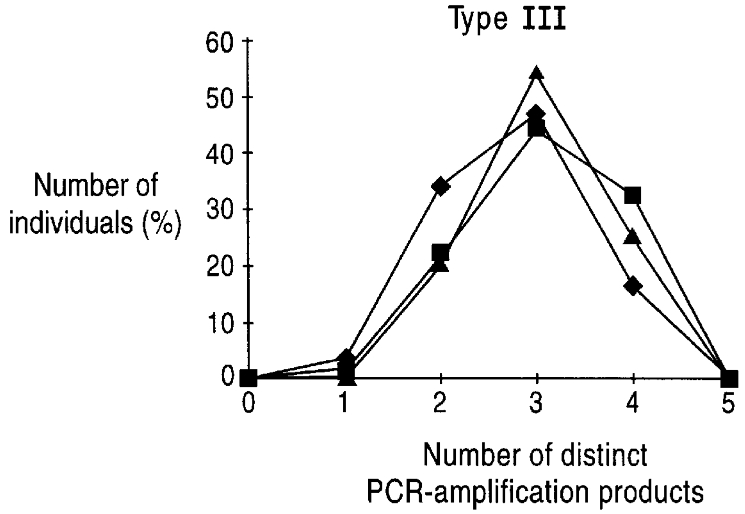
Figures 1, 5A:
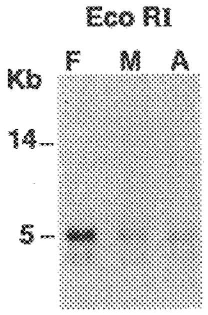
Figures 2, 5A:
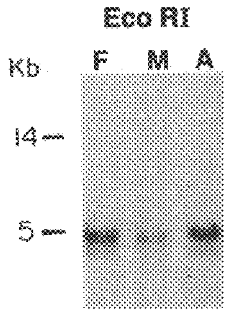
Figures 3, 5A:
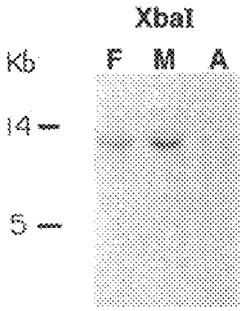
Figure 5C:
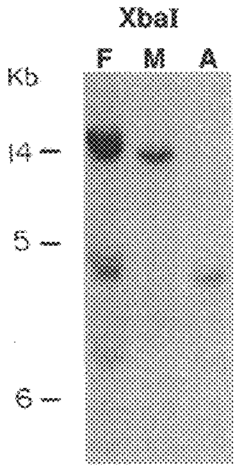
Figures 1, 5B:
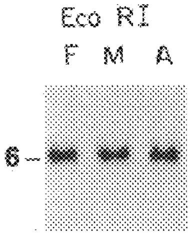
Figures 2, 5B:
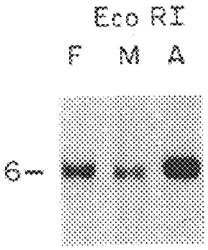
Figures 3, 5B:
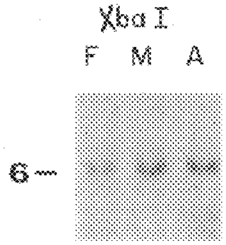

FIG. 3: Number of distinct PCR amplification products revealed by the marker C272 in the patients, their parents and controls.

A total of 90 type I patients, 81 type II patients, 30 type III patients, their parents and 59 controls were studied. The number of distinct PCR amplification products are shown as abscissae, the number of individual tested (%) as ordinates. ♦:affected. ■:parents, ▲: controls.

FIG. 4: Proof of the existence of deletions occurring de novo detected with the microsatellite C161 in affected type I patients.

4*a*. The segregation of the alleles detected with the marker C272 neither proves nor rules out the existence of deletions in the families 8, 9 and 10. It is noted that the patients display only a single PCR amplification product.

4*b*. The segregation of the alleles detected with the marker C161 reveals the existence of deletions occurring de novo in the families 8 and 9, since the affected child has received only a single locus from its parents (family 8) or from its father (family 9). In the family 10, the detection of six distinct PCR amplification products rules out any possibility of a deletion removing one of the three loci detected with C161.

F: father, M: mother, A: affected. The points indicate the alleleic fragments.

FIG. 5: Analysis of the restriction fragment length polymorphism (RFLP) and of the gene dosage at the locus detected with the phage L-132 in patients affected by a type I SMA. The genetic analysis was carried out after digestion of the DNA either with EcoR I (families 6 and 7) or with Xba I (families 3 and 5). The membranes were hybridized with the clone L-132 5a and the probe JK53 5b. The gene dosage was determined by densitometric examination of the hybridization signal for the families 3, 6 and 7. In the family 6, the intensity of the band is reduced by 50% in the mother and the affected child, indicating that an inherited deletion is responsible. In the families 7 and 3, the intensity of the band from the affected children is markedly weaker than that of the parents, suggesting that the deletion has occurred de novo. In the family 5, the analysis of the RFLP detected with the enzyme Xba I shows that the affected child has not received an allele from its mother.

REFERENCES

1. Pearn J. 1980. Classification of spinal muscular atrophies. *Lancet;* 1:919–922.
2. Munsat T L. 1991. Workshop report. International SMA collaboration. Neuromuscular Disorders; 1:81.
3. Brzustowicz L M, Lehner T, Castilla L H, Penchaszadeh G K, Wilhelmsen K C, Daniels R et al. 1990. Genetic mapping of chronic childhood-onset spinal muscular atrophy to chromosome 5q11.2–q13.3. *Nature;* 344:540–541.
4. Melki J, Abdelhak S, Sheth P, Bachelot M F, Burlet P, Marcadet A et al. 1990. Gene for chronic proximal spinal muscular atrophies maps to chromosome 5*q*. *Nature;* 344:764–768.
5. Gilliam T C, Brzustowicz L M, Castilla L M, Lehner T, Penchaszadeh G K, Daniels R J et al. 1990. Genetic homogeneity between acute and chronic forms of spinal muscular atrophy. *Nature;* 345:823–825.
6. Melki J, Sheth P, Abdelhak S, Burlet P, Bachelot M F, Lathrop G M et al. 1990. Mapping of acute (type I) spinal muscular atrophy to chromosome 5q12–q14. *Lancet;* 336:271–273.
7. Clermont O, Burlet P, Burglen L, Lefebvre S, Pascal F, Weissenbach J et al. 1994. Use of genetic and physical mapping to locate the spinal muscular atrophy locus between two new highly polymorphic DNA markers. *AM J Hum Genet.;* 54:687–694.
8. Green E. D and Olson M. V. 1990. *Proc. Natl. Acad. Sci. USA*. 87,213.
9. Hazan J, Dubay C, Pankowiak M P, Becuwe N, Weissenbach J. 1992. A genetic linkage map of human chromosome 20 composed entirely of microsatellite markers. *Genomics;* 12:183–189.

10. Smith L M, Sanders J Z, Kaiser R J, Hughes P, Dodd C, Connell C R et al. 1986. Fluorescence detection in automated DNA sequence analysis. *Nature;* 321:674–679.
11. Carlock L. R, Sharecky D., Dana S. 1985. *Am. J. Hum. Genet.* 37.839.
12. Chumakov I M, Le Gall I, Billault A, Ougen P, Soularue P, Guillou S et al. 1992. Isolation of chromosome 21—specific yeast artificial chromosomes from a total human genome library. *Nature Genetics;* 1:222–226.
13. Klein P. W, Wang C. H, Lyndon L. L, Vitale E, Pan J et al. 1993. Construction of a yeast artificial chromosome contig spanning the spinal muscular atrophy disease gene region. *Proc. Natl. Acad. Sci. USA;* 90:6801–6805.
14. Francis M. J, Morrison K. E, Campbell L, Grewal P. K, Christodoulou Z et al. 1993. A contig of non-chimaeric YACs containing the spinal muscular atrophy gene in 5q13.*Human Molecular Genetics.* 8:1161–1167.
15. Munsat T. L. (1991). Workshop report. International SMA collaboration. Neuromuscular Disorders 1, 81
16. Brzustowicz L. M., Lehner T., Castilla L. H., Penchaszadeh G. K., Wilhelmsen K. C., Daniels R. et al. (1990). Genetic mapping of chronic childhood-onset spinal muscular atrophy to chromosome 5q11.2–q13.3. *Nature* 344, 540–541
17. Melki J., Abdelhak S., Sheth P., Bachelot M. F., Burlet P., Marcadet A. et al. (1990). Gene for proximal spinal muscular atrophies maps to chromosome 5q. Nature 344, 764–768
18. Gilliam T. C., Brzustowicz L. M., Castilla L. H., Lehner T., Penchaszadeh G. K., Daniels R. et al. (1990). Genetic homogeneity between acute and chronic forms of spinal muscular atrophy. *Nature* 345, 823–825
19. Melki J., Sheth P., Abdelhak S., Burlet P., Bachelot M. F., Lathrop G. M. et al. (1990). Mapping of acute (type I) spinal muscular atrophy to chromosome 5q12–q14. *Lancet* 336, 271–273.
20. Hazan J., Dubay C., Pankowiak M. P., Becuwe N. and Weissenbach J. (1992). A genetic linkage map of human chromosome 20 composed entirely of microsatellite markers. *Genomics* 12, 183–189
21. Clermont O., Burlet P., Burglen L., Lefebvre S., Pascal F., Mc Pherson J., Wasmuth J. J., Cohen D., Le Paslier D., Weissenbach J., Lathrop M., Munnich A. and Melki J. (1994). Use of genetic and physical mapping to locate the spinal muscular atrophy locus between two new highly polymorphic DNA markers. *Am. J. Hum. Genet* 54, 687–694
22. Burlet P., Clermont O., Lefebvre S., Bürglen L., Millasseau P., Reboullet S., Bénichou B., Zeviani M., Le Paslier D., Cohen D., Weissenbach J., Munnich A. and Melki J. (1994). Construction d'un contig de chromosomes artificiels de levure couvrant le locus des amyotrophies spinales infantiles [Construction of a yeast artificial chromosome contig covering the infantile spinal muscular atrophy locus]. *C. R. Acad. Sci.* (submitted for publication)
23. Melki J., Lefebvre S., Bürglen L., Burlet P., Clermont O., Millasseau P., Reboullet S., Bénichou B., Zeviani M., Le Paslier D., Cohen D., Weissenbach J. and Munnich A. (1994). De novo and inherited deletions of the 5q13 region in spinal muscular atrophies. *Science*. (in press)
24. Carlock L. R., Skarecky D., Dana S. L. et Wasmuth J. J. (1985). Deletion mapping of human chromosome 5 using chromosome-specific DNA probes. *Am. J. Hum. Genet* 37, 839–852
25. Monaco A. P., Bertelson C. J., Liechti-Gallati S., Moser H. et Kunkel L. M. (1988). An explanation for the phenotypic differences between patients bearing partial deletions of the DMD locus. *Genomics* 2, 90–95
26. Hausmanowa-Petrusewicz I., Zaremba I. et Borkowska J. (1985). Chronic proximal spinal muscular atrophy of childhood and adolescence: problems of classification and genetic counselling. *J. Med. Genet* 22, 350–353
27. Zerres K. (1988). Genetik spinaler muskelatrophien [Genetics of spinal muscular atrophies]. Habilitationsschrift Universität Bonn.
28. Daniels R. J., Tomas N. H., MacKinnon R. N., Lehner T., Ott J., Flint T. J. et al. (1992). Linkage analysis of spinal muscular atrophy. *Genomics* 12, 335–339

---

We claim:

1. An isolated nucleic acid fragment, wherein said nucleic acid fragment consists of a sequence selected from:

a) SEQ ID NOS: 1, 2, 3, 4 and 5, b) a fragment of at least 12 contiguous nucleotides of SEQ ID NOS: 1, 2, 3 and 5, and;

c) a sequence fully complementary to the sequences a) or b).

2. The nucleic acid fragment of claim 1, wherein said fragment is selected from SEQ ID NOS:6–23.

3. An isolated nucleic acid, consisting of a nucleic acid of claim 1 or 2 linked to a nucleic acid which does not hybridize to a human DNA.

4. A pair of primers, comprising:

a) a first primer containing at least 12 contiguous nucleotides of SEQ ID NO:6 or of a sequence fully complementary to SEQ ID NO:6, and b) a second primer containing at least 12 contiguous nucleotides of SEQ ID NO:7 or of a sequence fully complementary to SEQ ID NO:7.

5. The pair of primers of claim 4, wherein said first primer consists of a nucleic acid of SEQ ID NO: 16 and said second primer consists of a nucleic acid of SEQ ID NO: 17.

6. A pair of primers, comprising:

a) a first primer containing at least 12 contiguous nucleotides of SEQ ID NO:8 or of a sequence fully complementary to SEQ ID NO:8 and b) a second primer containing at least 12 contiguous nucleotides of SEQ ID NO:9 or of a sequence fully complementary to SEQ ID NO:9.

7. The pair of primers of claim 6, wherein said first primer consists of a nucleic acid of SEQ ID NO: 18 and said second primer consists of a nucleic acid of SEQ ID NO: 19.

8. A pair of primers, comprising:

a) a first primer containing at least 12 contiguous nucleotides of SEQ ID NO:12 or of a, sequence fully complementary to SEQ ID NO:12, and b) a second primer containing at least 12 contiguous nucleotides of SEQ ID NO:13 or of a sequence fully complementary to SEQ ID NO:13.

9. The pair of primers of claim 8, wherein said first primer consists of a nucleic acid of SEQ ID NO: 20 and said second primer consists of a nucleic acid of SEQ ID NO: 21.

10. A pair of primers, comprising:

a) a first primer containing at least 12 contiguous nucleotides of SEQ ID NO:14 or of a sequence fully complementary to SEQ ID NO:14, and b) a second primer containing at least 12 contiguous nucleotides of SEQ ID NO:15 or of a sequence fully complementary to SEQ ID NO:15.

11. The pair of primers of claim 10, wherein said first primer consists of a nucleic acid of SEQ ID NO:22 and said second primer consists of a nucleic acid of SEQ ID NO: 23.

12. A pair of primers, comprising:

a) a first primer containing at least 12 contiguous nucleotides of SEQ ID NO:10 or of a sequence fully complementary to SEQ ID NO:10, and b) a second primer containing at least 12 contiguous nucleotides of SEQ ID NO:11 or of a sequence fully complementary to SEQ ID NO:11.

13. A nucleic acid probe, comprising the nucleic acid of claim 1 and a label.

14. A method of detection of an alteration in the human chromosome 5q13 region in a sample, comprising contacting the sample with a nucleic acid of claim 1, determining the pattern of hybridization between said sample and said nucleic acid, said pattern being correlated to the presence or absence of an alteration in said chromosome.

15. A method of detection of an alteration in the human chromosome 5q13 region in a sample, comprising (i) performing an amplification reaction of the sample using a pair of primers according to any one of claims 4 to 12, and (ii) analyzing the amplification products obtained in (i), said amplification products being correlated to the presence or absence of an alteration in said chromosome.

16. The method of claim 15, wherein the analyzing is performed by eletrophoretic gel migration.

* * * * *

SEQUENCE LISTING

```
(1) GENERAL INFORMATION:

   (iii) NUMBER OF SEQUENCES: 23


(2) INFORMATION FOR SEQ ID NO: 1:

     (i) SEQUENCE CHARACTERISTICS:
          (A) LENGTH: 372 base pairs
          (B) TYPE: nucleotide
          (C) STRANDEDNESS: double
          (D) TOPOLOGY: linear

    (ii) MOLECULE TYPE: DNA (genomic)

   (iii) HYPOTHETICAL: NO

    (iv) ANTI-SENSE: NO

    (vi) ORIGINAL SOURCE:
          (A) ORGANISM: Homo sapiens

    (xi) SEQUENCE DESCRIPTION: SEQ ID NO: 1:

ACCTGANCCC AGANGGTCAA GGCTGCAGTG AGACGAGATT GCNCCACTGC CCTCCACCCT      60
```

-continued

```
GGGTGATAAG AGTGGGACCC TGTNTCAAAA CATACACACA CACACACACA CACACACACA    120

CACACACACA CACACTCTCT CTCTCTCTCT CTCTCTCTCT CTCTCTCTCT CTCTCTCTCA    180

AAAACACTTG GTCTGTTATT TTTNCGAAAT TGTCAGTCAT AGTTATCTGT TAGACCAAAG    240

CTGNGTAAGN ACATTTATTA CATTGCCTCC TACAACTTCA TCAGCTAATG TATTTGCTAT    300

ATAGCAATTA CATATNGGNA TATATTATCT TNAGGGGATG GCCANGTNAT AAAACTGTCA    360

CTGAGGAAAG GA                                                        372
```

(2) INFORMATION FOR SEQ ID NO: 2:

(i) SEQUENCE CHARACTERISTICS:
(A) LENGTH: 294 base pairs
(B) TYPE: nucleotide
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 2:

```
CCTCCCACCT NAGCCTCCCC AGTAGCTAGG ACTATAGGCG TGCNCCACCA AGCTCAGCTA     60

TTTTTNNTAT TTAGTAGAGA CGGGGTTTCG GCANGCTTAG GCCTCGTNTC GAACTCCAGT    120

GTGTGTGTGT GTGTGTGTGT GTGTGTGTGT GTGTGTGTGT GTGTGTGTGT AGATATTTAT    180

TCCCCCTCCC CCTTGGAAAA GTAAGTAAGC TCCTACTAGG AATTTAAAAC CTGCTTGATC    240

TATATAAAGA CAAACAAGGA AAGACAAACA TGGGGGCAGG AAGGAAGGCA GATC          294
```

(2) INFORMATION FOR SEQ ID NO: 3:

(i) SEQUENCE CHARACTERISTICS:
(A) LENGTH: 141 base pairs
(B) TYPE: nucleotide
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 3 :

```
TCGAGGTAGA TTTGTATTAT ATCCCATGTA CACACACACA CACACACACA CACACACACA     60

CACACACAGA CTTAATCTGT TTACAGAAAT AAAAGGAATA AAATACCGTT TCTACTATAC    120

ACCAAAACTA GCCATCTTGA C                                              141
```

(2) INFORMATION FOR SEQ ID NO: 4:

(i) SEQUENCE CHARACTERISTICS:
(A) LENGTH: 305 base pairs
(B) TYPE: nucleotide
(C) STRANDEDNESS: double
(D) TOPOLOGY: linear (ii) MOLECULE TYPE: DNA (genomic)

-continued (iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 4:

CCCTGAGAAG GCTTCCTCCT GAGTATGCAT AAACATTCAC AGCTTGCATG CGTGTGTGTG 60

TGTGTGTGTG TGTGTATGTT TGCTTGCACT GTAAAAACAA TTGCAACATC AACAGAAATA 120

AAAATTAAAG GAATAATTCT CCTCCGACTC TGCCGTTCCA TCCAGTGAAA CTCTTCATTC 180

TGGGGTAAAG TTCCTTCAGT TCTTTCATAG ATAGGTATAT ACTTCATAAG TCAAACAATC 240

AGGCTGGGTG CAGTAGCTCA TGCCTGTAAT CCCAGCCCTT TGGGAGGCCG AGCTGGGCAG 300

ATCGA 305

(2) INFORMATION FOR SEQ ID NO: 5:

(i) SEQUENCE CHARACTERISTICS:
(A) LENGTH: 350 base pairs
(B) TYPE: nucleotide
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 5:

TCCACCCGCC TTGGCCTCCC AAAGCNCTGG GATTACAGGC GTGACTGCCG CACCCAGCTG 60

TAAACTGGNT TNNTAATGGT AGATTTTNAG GTATTAACAA TAGATAAAAA GATACTTTTN 120

GGCATACTGT GTATTGGGAT GGGGTTAGAA CAGGTGTNCT ACCCAAGACA TTTACTTAAA 180

ATCGCCCTCG AAATGCTATG TGAGCTGTGT GTGTGTGTGT GTGTGTGTGT GTATTAAGGA 240

AAAGCATGAA AGTATTTATG CTTGATTTTT TTTTTTNACT CATAGCTTCA TAGTGGANCA 300

GATACATAGT CTAAATCAAA ATGTTTAAAC TTTTTATGTC ACTTGCTGTC 350

(2) INFORMATION FOR SEQ ID NO: 6:

(i) SEQUENCE CHARACTERISTICS:
(A) LENGTH: 94 base pairs
(B) TYPE: nucleotide
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 6:

ACCTGANCCC AGANGGTCAA GGCTGCAGTG AGACGAGATT GCNCCACTGC CCTCCACCCT 60

GGGTGATAAG AGTGGGACCC TGTNTCAAAA CATA 94

-continued (2) INFORMATION FOR SEQ ID NO: 7:

(i) SEQUENCE CHARACTERISTICS:
(A) LENGTH: 194 base pairs
(B) TYPE: nucleotide
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 7:

CAAAAACACT TGGTCTGTTA TTTTTNCGAA ATTGTCAGTC ATAGTTATCT GTTAGACCAA 60

AGCTGNGTAA GNACATTTAT TACATTGCCT CCTACAACTT CATCAGCTAA TGTATTTGCT 120

ATATAGCAAT TACATATNGG NATATATTAT CTTNAGGGGA TGGCCANGTN ATAAAACTGT 180

CACTGAGGAA AGGA 194

(2) INFORMATION FOR SEQ ID NO: 8:

(i) SEQUENCE CHARACTERISTICS:
(A) LENGTH: 118 base pairs
(B) TYPE: nucleotide
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 8:

CCTCCCACCT NAGCCTCCCC AGTAGCTAGG ACTATAGGCG TGCNCCACCA AGCTCAGCTA 60

TTTTTNNTAT TTAGTAGAGA CGGGGTTTCG GCANGCTTAG GCCTCGTNTC GAACTCCA 118

(2) INFORMATION FOR SEQ ID NO: 9:

(i) SEQUENCE CHARACTERISTICS:
(A) LENGTH: 124 base pairs
(B) TYPE: nucleotide
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 9:

AGATATTTAT TCCCCCTCCC CCTTGGAAAA GTAAGTAAGC TCCTACTAGG AATTTAAAAC 60

CTGCTTGATC TATATAAAGA CAAACAAGGA AAGACAAACA TGGGGGCAGG AAGGAAGGCA 120

GATC 124

(2) INFORMATION FOR SEQ ID NO: 10:

-continued (i) SEQUENCE CHARACTERISTICS:
(A) LENGTH: 30 base pairs
(B) TYPE: nucleotide
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 10:

TCGAGGTAGA TTTGTATTAT ATCCCATGTA 30

(2) INFORMATION FOR SEQ ID NO: 11:

(i) SEQUENCE CHARACTERISTICS:
(A) LENGTH: 71 base pairs
(B) TYPE: nucleotide
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 11:

CTTAATCTGT TTACAGAAAT AAAAGGAATA AAATACCGTT TCTACTATAC ACCAAAACTA 60

GCCATCTTGA C 71

(2) INFORMATION FOR SEQ ID NO: 12:

(i) SEQUENCE CHARACTERISTICS:
(A) LENGTH: 51 base pairs
(B) TYPE: nucleotide
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 12:

CCCTGAGAAG GCTTCCTCCT GAGTATGCAT AAACATTCAC AGCTTGCATG C 51

(2) INFORMATION FOR SEQ ID NO: 13:

(i) SEQUENCE CHARACTERISTICS:
(A) LENGTH: 230 base pairs
(B) TYPE: nucleotide
(C) STRANDEDNESS: double
(D) TOPOLOGY: linear (ii) MOLECULE TYPE: DNA (genomic)

(iii) HYPOTHETICAL: NO

-continued (iv) ANTI-SENSE: NO (vi) ORIGINAL SOURCE:
(A) ORGANISM: Homo sapiens (xi) SEQUENCE DESCRIPTION: SEQ ID NO: 13:

ATGTTTGCTT GCACTGTAAA AACAATTGCA ACATCAACAG AAATAAAAAT TAAAGGAATA 60

ATTCTCCTCC GACTCTGCCG TTCCATCCAG TGAAACTCTT CATTCTGGGG TAAAGTTCCT 120

TCAGTTCTTT CATAGATAGG TATATACTTC ATAAGTCAAA CAATCAGGCT GGGTGCAGTA 180

GCTCATGCCT GTAATCCCAG CCCTTTGGGA GGCCGAGCTG GGCAGATCGA 230

(2) INFORMATION FOR SEQ ID NO: 14:

(i) SEQUENCE CHARACTERISTICS:
(A) LENGTH: 206 base pairs
(B) TYPE: nucleotide
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 14:

TCCACCCGCC TTGGCCTCCC AAAGCNCTGG GATTACAGGC GTGACTGCCG CACCCAGCTG 60

TAAACTGGNT TNNTAATGGT AGATTTTNAG GTATTAACAA TAGATAAAAA GATACTTTTN 120

GGCATACTGT GTATTGGGAT GGGGTTAGAA CAGGTGTNCT ACCCAAGACA TTTACTTAAA 180

ATCGCCCTCG AAATGCTATG TGAGCT 206

(2) INFORMATION FOR SEQ ID NO:15:

(i) SEQUENCE CHARACTERISTICS:
(A) LENGTH:118 base pairs
(B) TYPE: nucleotide
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 15:

ATTAAGGAAA AGCATGAAAG TATTTATGCT TGATTTTTTT TTTTNACTCA TAGCTTCATA 60

GTGGANCAGA TACATAGTCT AAATCAAAAT GTTTAAACTT TTTATGTCAC TTGCTGTC 118

(2) INFORMATION FOR SEQ ID NO: 16:

(i) SEQUENCE CHARACTERISTICS:
(A) LENGTH: 20 base pairs
(B) TYPE: nucleotide
(C) STRANDEDNESS: single
(D) TOPOLOGY: linear (ii) MOLECULE TYPE: DNA (genomic)

(iii) HYPOTHETICAL: NO

-continued (iv) ANTI-SENSE: NO (vi) ORIGINAL SOURCE:
(A) ORGANISM: Homo sapiens (xi) SEQUENCE DESCRIPTION: SEQ ID NO: 16:

CCTCCACCCT GGGTGATAAG 20

(2) INFORMATION FOR SEQ ID NO: 17:

(i) SEQUENCE CHARACTERISTICS:
(A) LENGTH: 21 base pairs
(B) TYPE: nucleotide
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 17:

GCTGATGAAG TTGTAGGAGG C 21

(2) INFORMATION FOR SEQ ID NO: 18:

(i) SEQUENCE CHARACTERISTICS:
(A) LENGTH: 20 base pairs
(B) TYPE: nucleotide
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 18:

TAGAGACGGG GTTTCGGCAT 20

(2) INFORMATION FOR SEQ ID NO: 19:

(i) SEQUENCE CHARACTERISTICS:
(A) LENGTH: 19 base pairs
(B) TYPE: nucleotide
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 19:

GATCTGCCTT CCTTCCTGC 19

(2) INFORMATION FOR SEQ ID NO: 20:

-continued (i) SEQUENCE CHARACTERISTICS:
(A) LENGTH: 20 base pairs
(B) TYPE: nucleotide
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 20:

GGCTTCCTCC TGAGTATGCA 20

(2) INFORMATION FOR SEQ ID NO: 21:

(i) SEQUENCE CHARACTERISTICS:
(A) LENGTH: 20 base pairs
(B) TYPE: nucleotide
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 21:

GTTTCACTGG ATGGAACGGC 20

(2) INFORMATION FOR SEQ ID NO: 22:

(i) SEQUENCE CHARACTERISTICS:
(A) LENGTH: 20 base pairs
(B) TYPE: nucleotide
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Homo sapiens (xi) SEQUENCE DESCRIPTION: SEQ ID NO: 22:

ATCGCCCTCG AAATGCTATG 20

(2) INFORMATION FOR SEQ ID NO: 23:

(i) SEQUENCE CHARACTERISTICS:
(A) LENGTH: 21 base pairs
(B) TYPE: nucleotide
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:

-continued

```
        (A) ORGANISM: Homo sapiens

    (xi) SEQUENCE DESCRIPTION: SEQ ID NO: 23:

CTGTTCCACT ATGAAGCTAT G                                           21
```